United States Patent [19]
Irie et al.

[11] Patent Number: 5,626,605
[45] Date of Patent: *May 6, 1997

[54] THROMBOSIS FILTER

[75] Inventors: Toshiyuki Irie; Shigeru Frui, both of Tokorozawa, Japan

[73] Assignee: SciMed Life Systems, Inc., Maple Grove, Minn.

[*] Notice: The term of this patent shall not extend beyond the expiration date of Pat. No. 5,370,657.

[21] Appl. No.: 256,551

[22] PCT Filed: Dec. 30, 1992

[86] PCT No.: PCT/US92/11311

§ 371 Date: Jun. 27, 1994

§ 102(e) Date: Jun. 27, 1994

[87] PCT Pub. No.: WO93/15136

PCT Pub. Date: Aug. 5, 1993

Related U.S. Application Data

[63] Continuation of Ser. No. 42,424, Mar. 26, 1993, Pat. No. 5,370,657.

[30] Foreign Application Priority Data

Dec. 30, 1991 [JP] Japan ................. 3-113712 U

[51] Int. Cl.$^6$ ..................................... A61M 29/00
[52] U.S. Cl. .................. 606/200; 623/1; 623/12
[58] Field of Search ......................... 606/108, 191, 606/192, 194, 198, 200; 623/1, 12

[56] References Cited

U.S. PATENT DOCUMENTS

| | | |
|---|---|---|
| 3,334,629 | 8/1967 | Cohn . |
| 3,467,102 | 9/1969 | Fogarty et al. . |
| 3,540,431 | 11/1970 | Mobin-Uddin . |
| 3,868,956 | 3/1975 | Alfidi . |
| 3,952,747 | 4/1976 | Kimmell . |
| 4,425,908 | 1/1984 | Simon . |
| 4,430,081 | 2/1984 | Timmermans . |
| 4,494,531 | 1/1985 | Gianturco . |
| 4,619,246 | 10/1986 | Molgaard-Nielsen . |
| 4,643,184 | 2/1987 | Mobin-Uddin . |
| 4,650,456 | 3/1987 | Luther . |
| 4,662,885 | 5/1987 | DiPisa, Jr. . |
| 4,688,553 | 8/1987 | Metals . |

(List continued on next page.)

FOREIGN PATENT DOCUMENTS

| | | |
|---|---|---|
| 117940A2 | 9/1984 | European Pat. Off. . |
| 0270432B1 | 6/1988 | European Pat. Off. . |
| 0293605A1 | 12/1988 | European Pat. Off. . |
| 0350043B1 | 1/1990 | European Pat. Off. . |
| 472334A1 | 2/1992 | European Pat. Off. . |
| 2570288 | 3/1986 | France . |
| 2573646 | 5/1986 | France . |
| 2580504 | 10/1986 | France . |
| WO92/03097 | 3/1992 | WIPO . |

OTHER PUBLICATIONS

C. J. Grassi, "Inferior Vena Cava Filters: Analysis of Five Currently Available Devices," pp. 813–821, 1991, *AJR*, 156.
G.S. Dorfman, "Percutaneous Inferior Veno Cava Filters." pp. 987–992, 1990, *Radiology*, 174.
R. W. Gunter, H. Schild, A. Fries, and S. Storkel, "Vena Cava Filter to Prevent Pulmonary Embolism: Experimental Study," pp. 315–320, 1985, *Radiology*, 156.

(List continued on next page.)

*Primary Examiner*—Michael Powell Buiz
*Assistant Examiner*—William Lewis
*Attorney, Agent, or Firm*—Nawrocki, Rooney & Sivertson

[57] ABSTRACT

A thrombosis filter that has an improved filtering function and can be securely anchored at a desired location and be removed through an endovenous route even after the growth of neointima. The thrombosis filter of this invention includes a first and a second filtering and holding unit, each unit including a coupling mechanism at its outer extremity in the form of a hook, and a plurality of resilient struts that are biased into contact therewith with the vein wall. The units are interconnected by a core shaft which consists of a compression member and a pair of core wires.

15 Claims, 2 Drawing Sheets

U.S. PATENT DOCUMENTS

| | | |
|---|---|---|
| 4,727,873 | 3/1988 | Mobin-Uddin . |
| 4,781,177 | 11/1988 | Lebigot . |
| 4,793,348 | 12/1988 | Palmaz . |
| 4,817,600 | 4/1989 | Herms et al. . |
| 4,832,055 | 5/1989 | Palestrant . |
| 4,873,978 | 10/1989 | Ginsburg . |
| 4,957,501 | 9/1990 | Lahille et al. . |
| 4,969,891 | 11/1990 | Gewertz . |
| 4,990,156 | 2/1991 | Lefebvre . |
| 4,998,539 | 3/1991 | Delsanti . |
| 5,035,706 | 7/1991 | Giantureo . |
| 5,059,205 | 10/1991 | El-Nounou et al. . |
| 5,071,407 | 12/1991 | Termin . |
| 5,108,418 | 4/1992 | Lefebvre . |
| 5,108,419 | 4/1992 | Reger et al. . |
| 5,133,733 | 7/1992 | Rasmussen et al. . |
| 5,147,379 | 9/1992 | Sabbaghian et al. . |
| 5,152,777 | 10/1992 | Goldberg et al. . |
| 5,160,342 | 11/1992 | Reger et al. . |
| 5,234,458 | 8/1993 | Metais . |
| 5,242,462 | 9/1993 | El-Nounou et al. . |

OTHER PUBLICATIONS

G. Lund, J. Rysavy, E. Salomonowitz et al, "A New Vena Caval Filter for Percutaneous Placement and Retrieval: Experimental Study." pp. 369–372, 1984 *Radiology*, 152.

J. J. Alexander, B. L. Gewertz, Chien–Tai Lu and C. K. Zarins, "New Criteria for Placement of a prophylactic Vena Cava Filter." pp. 405–409, 1986 *Surgery Gynecology & Obstetrics*, 163.

P. J. Golueke, W. V. Garrett, J. E. Thompson et al, "Interruption of the Vena Cava by means of the Greenfield filter: Expanding the indications", pp. 111–117, 1988, *Surgery*, 103.

M. D. Darcy, T. P. Smith, D. W. Hunter et al, "Short–term Prophylaxis of Pulmonary Embolism by Using a Retrievable Vena Cava Filter.", pp. 836–838, 1986, *AJR*, 147.

M. H. Awh, F. C. Taylor and Chien–Tai Lu, "Spontaneous Fracture of a Vena–Tech Inferior Vena Caval Filter.", pp. 177–178, 1991, *AJR*, 157.

D. Kim, D. H. Porter, J. B. Siegel & M. Siman, "Perforation of the Inferior Vena Cava with Aortic and Vertebral Penetration by a Suprarenal Greenfield Filter.", pp. 721–723, 1989, *Radiology*, 172.

T. Irie, S. Furui, T. Yumauchi, K. Makita, S. Sawada, E. Takenaka, "Relocatable Gianturco Expandable Metallic Stents.", pp. 575–577, 1991, *Radiology*, 178.

A. M. Palestrant, P. Martin, M. Simon, "Comparative In Vitro Evaluation of the Nitinol Inferior Vana Cava Filter.", pp. 351–355, 1982, *Radiology*, 145.

M. Simon, A. M. Palestrant, "Transvenous Devices for the Management of Pulmonary Embolism.", pp. 308–318, 1980, Cardio Vascular and Interventional Radiology, 3.

G. Lund, J. Rysavy, D. W. Hunter, W. R. Castaneda–Zuniga, K. Amplatz, "Retrievable Vena Caval Filter Percutaneously Introduced.", p. 831, 1985, *Radiology*, 155.

A. Cragg, G. Lund, E. Salomonowitz, J. Rysavy, F. Castaneda, W. Castaneda–Zuniga, K. Amplatz, "A New Percutaneous Vena Cava Filter.", pp. 601–604, 1983, *AJR*, 141.

A. M. Fadali, S. R. Topaz, M. M. Ameli, V. I. Gott, "A filtering device for the prevention of particulate embolization during the course of cardiac surgery.", pp. 634–639, 1968, *Surgery*, 64.

Castaneda–Zuniga et al, "Seminars in Interventional Radiology." pp. 175–241, 1986, *Thieme Medical Publishers, Inc.*, 3.

M. J. Wallace, K. Ogawa, K. Wright, C. H. Carrasco, W. Richi, C. Charnasgavej, "Inferior Vena Caval Stent Filter.", pp. 1248–1250, 1986, *AJR*, 147.

U.S. Patent May 6, 1997 Sheet 1 of 2 5,626,605
Fig. 1
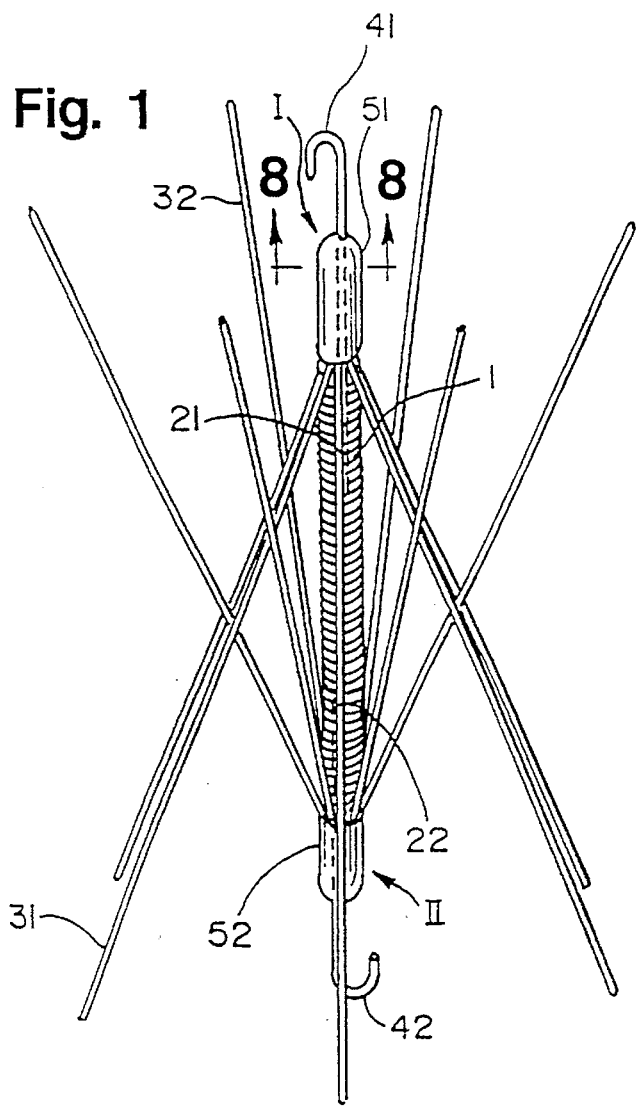
Fig. 2
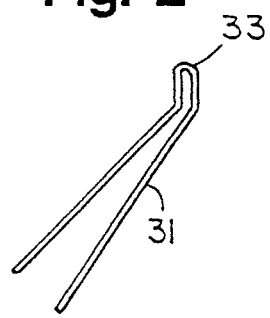
Fig. 3
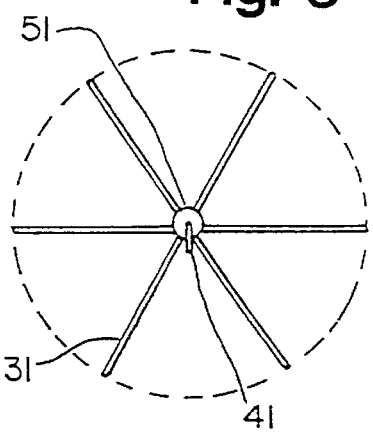
Fig. 8
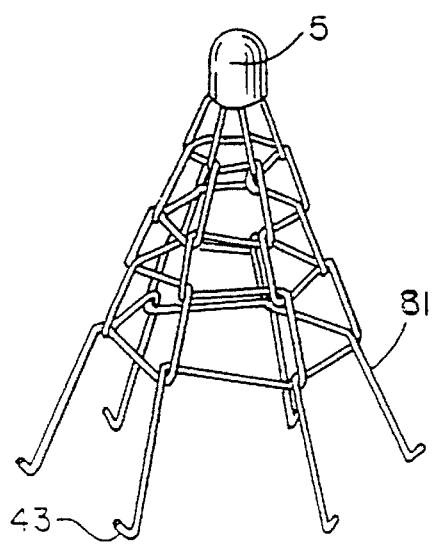
Fig. 9
PRIOR ART

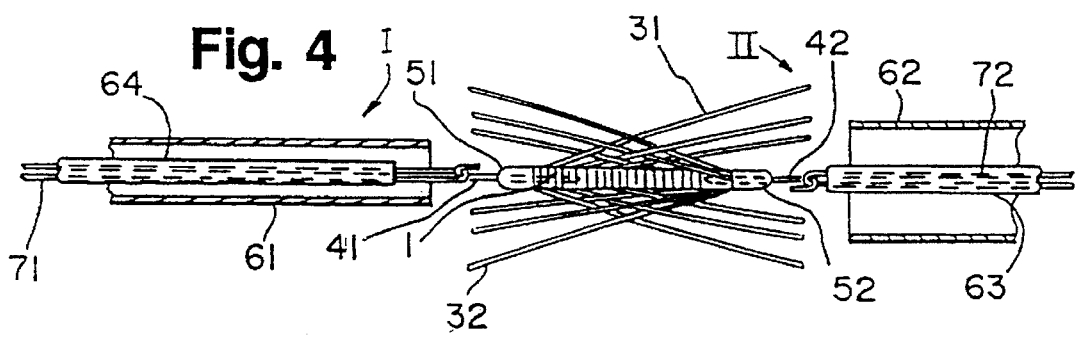
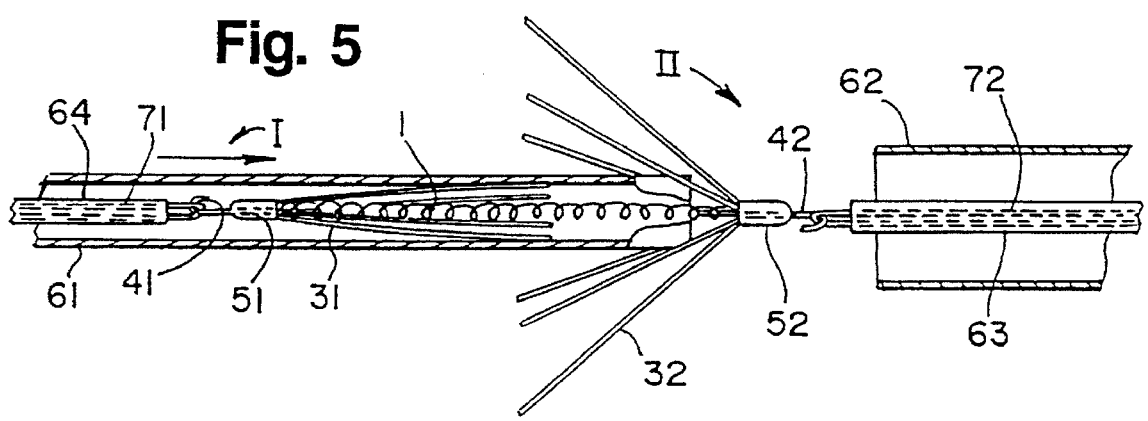
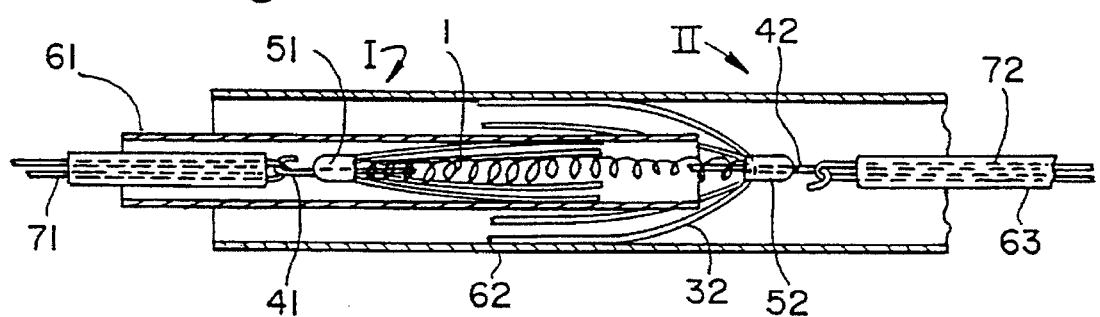
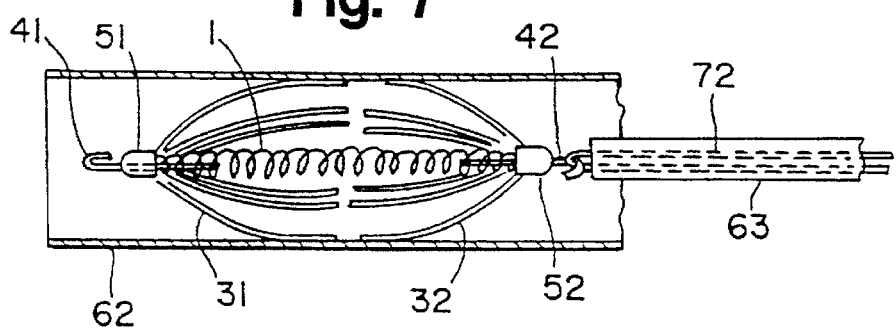

THROMBOSIS FILTER

This application is a continuation of application Ser. No. 08/042,424, filed Mar. 26, 1993, now U.S. Pat. No. 5,370,657.

BACKGROUND OF THE INVENTION

The present invention relates to thrombosis filters. To be more specific, it is about removable thrombosis filters which can be securely fixed at a selected location in the vascular system for trapping blood clots, and removed when desired such as when no longer required.

In recent years, pulmonary embolism has become an increasingly common medical emergency. Pulmonary embolisms may be caused by venous thrombosis that in turn may be caused by blood flow retention, venous intimal damage or coagulation abnormalities. Emergency or prophylactic treatments for these conditions include anticoagulant therapy, thrombolytic therapy, thrombectomy and inferior vena cava blocking procedures.

Among these therapeutic options, when an inferior vena cava blocking procedure is selected, one option is to perform a laparotomy under general anesthesia during which the inferior vena cava is ligated, sutured and shortened, or clipped. Another option is to intravenously insert a thrombosis filter into the inferior vena cava under local anesthesia. A laparotomy however, requires general anesthesia and is susceptible to thrombosis formation due to the discontinuation of anticoagulant therapy prior to surgery. For these reasons, percutaneous filter insertion is now more widely employed since it requires only local anesthesia.

Blood is returned to the heart from the lower part of the human body through the inferior vena cava and from the upper part of the body through the superior vena cava. The neck vein, known as the jugular vein, leads to the superior vena cava which is a vein that enters the upper part of the heart. A percutaneously inserted catheter that extends through the jugular vein and the superior vena cava and then into the heart can be manipulated to exit the heart through the mouth of the inferior vena cava into the heart. The inferior vena cava, a vein that enters the lower part of the heart, can also be accessed through the patients femoral vein. Thus, the inferior vena cava can be reached through two endovenous routes, both of which are available percutaneously.

A currently used percutaneous filter is shown in FIG. 9. The filter has anchors, 43, at the end of six struts, 81, with a head or central hub or fixation part, 5. One example of how this filter is used is to lead the filter within a capsule with the head of the filter introduced first if using the transfemoral vein approach or with the tail of it introduced first if using the transjugular vein approach. This type of filter possesses hooks at the end of the struts that impinge the inner wall of the blood vessel in order to ensure its firm fixation at the time of insertion. It is released from the capsule and expands within the inferior vena cava where it function as thrombosis filter.

Filters of the type shown in FIG. 9 perform the desired filtering function, requiring only local anesthesia for insertion. This has contributed to the high usage of the filter. A filter of the type shown in FIG. 9 is disclosed in U.S. Pat. No. 4,817,600. Approximately two to three weeks after insertion of this type of filter, neointima grows around the filter and its anchors to the inner wall of the blood vessel, which becomes an obstacle to the removal of the filter after its function has been fulfilled. Furthermore, this filter was not designed or intended to be removed. Since the need for a thrombosis filter, in many patients, is temporary, it may be desirable to remove the filter when it is no longer needed. In the prior art devices, such removal can be preformed surgically which exposes the patient to the usual risk and trauma associated with surgery. Thus there is a need for a thrombosis filter that can be removed without surgery.

The subject invention fulfills the need of a medical filter which can be non-surgically removed even after neointima has developed. As a result of this invention, a medical filter has been developed which includes insertion and removal accessories that enable the goal to be achieved. The filter of this invention includes a filtering portion that is permeable to the blood flow but which will filter out emboli and thrombus and will also hold the filter firmly in a selected location and permit removal through an endovenous route. The filtering and holding device of this medical filter includes two filter units that face each other and do not have hooks that impinge the inner wall of the blood vessel, in the same manner as the prior art filters, in order to anchor the device in the blood vessel.

The objective of this invention, therefore, is to provide thrombosis filters with a favorable filtering function which can be securely anchored at a desired location and be removed through an endovenous route even after the growth of neointima.

SUMMARY OF THE INVENTION

The above-mentioned objective is achieved by a thrombosis filter which is characterized by the following structure. The thrombosis filter of this invention includes a first and a second filtering and holding unit each unit including a coupling mechanism in the form of a hook. Each unit has a plurality of resilient struts which radiate from a central hub and lies on the surface of a cone. The units are interconnected by a core shaft which consists of a compression spring and a pair of core wires. The term compression spring means a spring that will draw the filtering and holding units toward each other to thereby minimize the overall longitudinal length of the filter. Inside the core shaft, there are core wires that are anchored in the units and have free ends which extend from their anchored ends toward the other unit. The struts are resilient and their free ends bear against the inner wall of the vein. However, the free ends do not include anchoring hooks, of the type disclosed in the prior art, that impinge the wall of the vein as does the above discussed prior art filter. The anchoring of the filter, of this invention, is accomplished by orientating the two filter units in opposite directions. The force from the compression springs pulls the hubs from the two units toward each other, which tends to open the struts of both units thus forcing their free ends into the wall of the vein and holding the filter in its selected location. More specifically, the core shaft of the upper unit (as seen in FIG. 1) consists of multiple struts which spread radially in an expansive direction while the core shaft of the lower unit consists of multiple struts which spread radially. The struts from the first and second units cross each other between their hubs and free ends, which when considering the conical surfaces that the struts lie upon, defines a V-shaped circular filtering grove. This V-shaped circular filtering groove is permeable to the flow of blood and performs an improved filtering function.

Although materials of the present thrombosis filters are not particularly restricted, it is desirable to use a flexible material that will return to its original shape after being deformed such as identity elastic alloy wire, high elastic alloy wire such as stainless steel, tungsten, platinum, piano wire, shape memory alloy wire, super elastic metal wire and chromium alloy. It is important that the coupling mechanisms in the form of hooks and the cord be constructed of material such a tungsten, platinum or gold that can be seen on a fluoroscope, to aid in the process of securing the coupling mechanisms.

Multiple number of struts or thrombosis filtering wires used for the present invention are divided into two units and are placed and anchored around their corresponding central hub at regular intervals to the extent possible. The struts of each unit lie on the surface of a cone with an anchoring part at the apex. The anchoring part is connected to and a part of the central hub.

Inside the compression spring, which constitutes the core shaft, a core wire extends from each of the filter units and function to reinforce the compression spring.

The angle between the radially spread struts and the core shaft can be optional, although it is preferable to maintain this angle within the range of 70 to 80 degrees.

The thickness of the wire constituting a strut is preferably 0.05 to 0.2 mm in diameter.

The ideal outside diameter of the compression spring is 0.5 to 2 mm in diameter, but there is no particular restriction to it. This diameter can of course be determined by the particular use intended for the filter.

As for the size of the thrombosis filters, there is no particular restriction. The size can be changed at one's discretion depending on the site of its application.

The present invention enables thrombosis filtering through multiple struts which spread radially. As a result the filtering and holding device is flexible in its radial dimension and can be compressed or collapsed radially for insertion, travel and removal. Since the struts do not have hooks for impinging the inner wall of the blood vessel, even when the struts are covered by neointima, they can be easily removed by pulling them towards the head or central hub. The compression spring, which serves as the core shaft, provides a core shaft that is flexible and facilitates maneuvering the filter units into the recovery tubes for removal. The compression spring allows relative movement of the units along the filter's longitudinal axis.

The core wires within the compression spring function to maintain the core shaft along a central axis extending between the two filter units as well as to achieve a desired flexibility of the compression spring.

The coupling mechanism, in the form of a hook element provided at the head of each filter unit, functions to connect the unit to mechanism that can be manipulated through an endovenous route at the time of removal.

As for the structure of the filter units facing each other, this arrangement serves to stabilize and anchor the filter inside the blood vessel and to prevent unfavorable phenomenon such as the displacement of the filter inside the vessels.

BRIEF DESCRIPTION OF THE DRAWINGS

FIG. 1 is a perspective view showing the thrombosis filter of this invention.

FIG. 2 is a perspective view showing a strut of the thrombosis filter of this invention.

FIG. 3 is an top view of filter unit I of the thrombosis filter of this invention.

FIG. 4 is a cross-sectional view illustrating a step in the method for removing the thrombosis filter of this invention from the patient.

FIG. 5 is a cross-sectional view illustrating a step in the method for removing the thrombosis filter of this invention from the patient.

FIG. 6 is a cross-sectional view illustrating a step in the method for removing the thrombosis filter of this invention from the patient.

FIG. 7 is a cross-sectional view illustrating a step in the method for removing the thrombosis filter of this invention from the patient.

FIG. 8 is a cross-section view of the head portion of the thrombosis filter of this invention taken along line 8—8 of FIG. 1.

FIG. 9 is a perspective view of a conventional prior art thrombosis filter.

DETAILED DESCRIPTION OF THE PREFERRED EMBODIMENT

The following is a discussion of how the present invention can be applied to a particular embodiment. This, however, does not mean that the application of the present invention is limited only to the following use.

FIG. 1 is a perspective view, of the filtering and holding device of the preferred embodiment of the present invention. The filter is fabricated mainly from stainless steel wires. The wire is 0.05 to 0.2 mm in diameter. The filter consists of twin units, I and II, that are spaced from each other along the filtering and holding device's longitudinal axis and which face each other and are connected by the compression spring 1.

The filter unit I includes the following structure. The upper end of core wire 21, as viewed in FIG. 1, extends downwardly from hook 41. Struts 31 also extend downwardly from hook 41 and spread radially in an expansive direction, centering around the core wire 21. The upper ends of struts 31 are fixed in the central hub or fixation part 51.

Filter unit II has the following structure. As viewed in FIG. 1, the core wire 22 and struts 32 extends upwardly from hook 42. Struts 32 spread radially at an angle to the filtering and holding device's longitudinal axis in an expansive direction, centering around the core wire 22. The struts 32 are anchored at, their lower end in central hub or fixation part 52.

The free ends of the struts for both units I and II are thus spring biased outwardly and can be forced inwardly to decrease the diameter of the filtering and holding device when it is located in the insertion and removal tubes.

As shall be discussed in greater detail, a welding or binder material is normally used for brazing the ends of the hooks 41 and 42 the core wires 21 and 22 the struts 31 and 32 and the ends of spring 1 to the central hub or fixation parts 51 and 52.

The filter units I and II are spaced from each other along the filtering and holding device's longitudinal axis such that struts 31 and 32 crossed each other at about their mid points. Hooks 41 and 42 are constructed of tungsten or stainless steel wires that have been bent into the shape shown in FIG. 1.

First ends of core wires 21 and 22 are connected to the central hub or fixation parts 51 and 52 along with the straight ends of hooks 41 and 42. The core wires 21 and 22 extend through the lumen formed by compression spring 1 and function as a core shaft that enhances the flexibility of compression spring 1. The other ends of core wires 21 and 22 are free.

FIG. 2 is a diagonal view of a strut 31 that includes a head 33. Strut 32 is identical to strut 33 and thus is not illustrated in an isolated view. The heads 33 of struts 31 and 32 become a part of the core shaft by being anchored in central hub or fixation parts 51 and 52.

FIG. 3 is a top view of filter unit I. As can be seen in this view, struts 31 emanate from the central core shaft and spread outwardly from this center in equal amounts into the surrounding area. Although six struts 31 in each filter unit have been found to be optimum, this number can be varied within the range of three to ten.

FIG. 8 includes two enlarged cross-sectional views taken through the central hub or fixation part 51. A tube 53 is used to form the central hub or fixation part 51 of the thrombosis filter. The straight end of hook 41, first end of core wire 21 and the heads 33 of struts 31 are all inserted into the tube 53. The ends of spring 1 could also be inserted into the tube 53 and bonded to the tube 53 or the ends could be fixed to the tube by welding or adhesive. A bonding material 54 is then introduced, while in a pliable stage, into tube 53 such that the bonding material 54 fills all the voids between the ends of the hook 41, core wire 21 and heads 33 within tube 53. When the pliable material 54 hardens the ends of the hook 41, core wire 21 and the heads 33 are all fixed in the central hub or fixation part 51. The tube 53 could remain as a permanent part of central hub or fixation part 51 or it could be removed.

It should be noted that the compression spring 1, hooks 41 and 42, core wires 21 and 22 and the struts 31 and 32 can all be fabricated from the same material or each of these parts could be fabricated from different material that will provide the desired characteristics for the particular part.

The following is an explanation of how this embodiment of the thrombosis filter is used. The thrombosis filter is dimensioned such that it can be stored in the distal end of a thin tube (2 to 3 mm in diameter). This insertion tube is percutaneously inserted into the patient and follows an endovenous route into the patient's inferior vena cava. This procedure is performed under local anesthesia. When the distal end of this tube reaches the target site, the filtering and holding device stored inside the tube is caused to exit the distal end of the tube where it become implanted in the patient's inferior vena cava. A pusher rod is extended through the insertion tube and is maneuverable from the proximate end of the insertion tube for expelling the filtering and holding device out the distal end of the insertion tube. It should be noted that the insertion procedure can be monitored on a fluoroscope.

The filtering and holding device after being released from the tube into the patient's inferior vena cava, through the above described procedure, is in the form as shown in FIG. 1. Within several week after the filtering and holding device has been implanted in the inferior vena cava, the struts 31 and 32, which are in contact with the inferior vena cava become covered by neointima.

When it becomes necessary or desirable to remove the filtering and holding device, the following procedure is followed. The term "medical filter" as used to describe and claim this embodiment includes in addition to the filtering and holding device the above mentioned insertion tube and the recovery hardware necessary to remove the filter. A recovery device is provided that can be inserted percutaneously and threaded through the endovenous route to the filtering and holding device. The recovery device includes a first tube 64, a second tube or sheath 61, a third tube 63 and a recovery tube or sheath 62.

Referring to FIG. 4, a doubled over cord 71 inserted through the proximal end of the first tube 64 such that the cord emerges at the distal end of the tube 64 and functions as a coupling mechanism in the form of a loop. The tube 64 then is passed through the second tube or sheath 61 which has been percutaneously inserted into the patient via the femoral vein such that its distal end is in the inferior vena cava of the patient adjacent the filtering and holding device. The tube 64 is advanced, through tube or sheath 61, to the filtering and holding device. The tube 64, that has the loop formed in cord 71 emerging from its distal end, is manipulated such that the coupling mechanism in the form of a loop is grasp by the complementary coupling mechanism in the form of a hook 41.

In the same manner, a doubled over cord 72 is passed through third tube 63 such that a loop that functions as a coupling mechanism emerges from the distal end of the tube. Third tube 63 is threaded through a recovery tube or sheath 62 which was percutaneously inserted through the right internal jugular vein such that its distal end is in the patients inferior vena cava. The third tube 63 is manipulated such that the coupling mechanism in the form of a loop is grasped by the complementary coupling mechanism in the form of a hook 42. After cord 64 is connected to hook 41 and cord 72 is connected to hook 42 the cords 64 and 72 are simultaneously pulled in opposite directions, causing units I and II to move away from each other. The compression spring 1 expands to permit this relative movement of units I and II. A tension is maintained on the cords 64 and 72 to insure that the connection between the cords 64 and 72 and the hooks 41 and 42 is maintained.

Cords 71 and 72 are made of or include radiopaque material such as stainless steel so the at the coupling of the loops with hooks 41 and 42 can be monitored on a scope.

The relative movement of units I and II has resulted in a corresponding movement of the struts 31 and 32 relative to the vessel wall and the filters have been freed from the neointima.

The next step in the process of removing the filtering and holding device from the patient is illustrated in FIG. 5. The cord 71 is pulled in its proximal direction to thus pull the filter unit 1 into tube or sheath 61 for temporary storage. Then tube 64 is advanced further through tube or sheath 61 to the point where its distal end is adjacent the ends of struts 32 that are secured in the fixation member 51 of unit II.

As can be best seen in FIG. 6, the next step in the removal procedure is to advance tube or sheath 62, in the direction toward its distal end, such that unit II and the distal end of tube or sheath 61 in which is stored unit I, are received within tube or sheath 62.

The entire filtering and holding device is now stored in recovery tube or sheath 62. By pulling one strand of cord 71, from its proximal end, cord 71 is released from hook 41 and can be removed from the patient. The second tube or sheath 61 can then be removed from the patient, and as shown in FIG. 7, and the entire filtering and holding device is now stored in recovery tube or sheath 62.

The final step in the process for removing the filtering and holding device from its resting place in the patient's inferior vena cava is to pull out the recovery tube or sheath 62.

When the filters used for the present invention are employed in vessels, in order to prevent the adhesion of thrombosis it is preferable to coat the filters with antithrombotic agents (such as heparin, urokinase and antithrombotic material including hydroxy methacrylate-styrene copolymer).

As a result of the thrombosis filters units I and II being connected by a compression spring with the struts 31 and 32 extending in opposite directions, fixation of the filtering and holding device at a selected location is accomplished upon release of the filter from the tube. In addition, the arrangement of the struts 31 and 32 extending in opposite directions and crossing provides a very effective thrombus filter. Moreover, the thrombus filter of this invention can be removed when the patient no longer has a need for it.

It is claimed:

1. A medical filter adapted to be percutaneously implanted, in and removed from a blood vessel having an inner wall, through an endovenous route via a tube, said medical filter comprising:

a filtering and holding device that extends along a longitudinal axis and is flexible in its radial dimension, said filtering and holding device being dimensioned such that it can be compressed radially into a collapsed condition in which it can be received in said tube and will open out and expand into biased engagement with the inner wall of said blood vessel when it emerges from the tube, said filtering and holding device including coupling mechanisms at both ends, said coupling mechanisms accessible through endovenous routes to enable the filtering and holding device to be seized, released from the inner wall of said blood vessel and withdrawn percutaneously from the blood vessel.

2. The invention as set forth in claim 1 wherein said medical filter includes first and second portions displaced longitudinally and joined by a resilient member that enables said first and second portions to move longitudinally relative to each other to facilitate releasing the first and second portions from the inner wall during removal.

3. The invention as set forth in claim 1 or 2 wherein said medical filter includes a recovery device that can be inserted percutaneously and threaded through an endovenous route such that its distal end is located at said filtering and holding device, and coupling mechanism carried by said recovery device at its distal end, said coupling mechanism carried by said recovery device being complementary to said coupling mechanism of said filtering and holding device such that said filtering and holding device can be seized by said recovery device.

4. The invention as set forth in claims 1 or 2 wherein said coupling mechanisms on the filtering and holding device are made of radiopaque material to assist in the process of snaring the filtering and holding device.

5. The invention as set forth in claim 3 wherein said medical filter includes a recovery tube having an open distal end dimensioned to receive the collapsed filtering and holding device, said recovery tube adapted to be inserted percutaneously into the patient and threaded over an endovenous route such that its open distal end is adjacent the filtering and holding device, said recovery device functioning to move the filtering and holding device from its location within the blood vessel to a location within the distal end of said recovery tube.

6. A filter to be placed in the blood vessel of a patient for trapping clots, the filter being inserted percutaneously through an insertion tube or tubes and expelled from the insertion tube or tubes at a selected location in the blood stream, where it implants itself in the inner wall of the blood vessel so as to prevent migration of the filter within the blood vessel, the filter comprising:

a first and a second unit that are spaced from each other along the filter's longitudinal axis, each of said units including a plurality of struts anchored such that their free ends radiate outwardly at an acute angle to said longitudinal axis in the direction toward the other of said units, said plurality of struts open out from a collapsed condition when the filter is released from the insertion tube or tubes into the blood vessel at the desired position causing the free ends to engage the inner wall of said blood vessel, one or more of said struts functioning to filter out clots that are flowing through the blood vessel, at least one of said struts having free ends that are forced into the side wall of the blood vessel as a result of a force attempting to move the filter axially of the blood vessel, at least one of said free ends functions as a holding device to anchor the filter at the desired position within the blood vessel, said insertion tube or tubes including a pusher that is maneuverable from the proximal end of the insertion tube or tubes for expelling the filter out the distal end of the insertion tube or tubes.

7. The invention as set forth in claim 6 wherein said first and second units are interconnected by a resilient member extending along said longitudinal axis, said resilient member exerting a force on said units causing the free ends of the struts to grip the inner wall of the blood vessel and hold the filter in its desired location.

8. A filter, having a longitudinal axis, to be placed in the blood vessel of a patient for trapping clots, said filter including struts that open out from a collapsed condition when it is released into the blood vessel of the patient at the desired position, said struts functioning to filter out clots that are flowing through the blood vessel and as holding devices to anchor the filter at the desired position within the blood vessel, said filter including first and second units that are spaced from each other along the filter's longitudinal axis, each of said units including a plurality of said struts anchored such that their free ends radiate outwardly at an acute angle to said longitudinal axis in the direction toward the other of said units such that the free ends to said struts engage the inner wall of said blood vessel, said first and second units being interconnected by an resilient member extending along said longitudinal axis, each end of said resilient member being connected to a unit, said resilient member exerting a force on said units causing the free ends of the struts to grip the inner wall of the blood vessel and thus anchor the filter in its desired position.

9. The invention as set forth in claim 8, wherein each unit of said filter includes a core wire, one end of each core wire is anchored to one of said units and extends from its anchor along said resilient member toward the other unit, said core wires terminating in free ends short of said other unit.

10. The invention as set forth in claims 8 or 9 wherein said filter includes a coupling mechanism at each of its ends, each of said coupling mechanisms being accessible percutaneously through the blood vessel in which the filter is implanted.

11. A method of recovering a filter, of the type that extends along the longitudinal axis of a blood vessel and includes coupling mechanisms at each of its ends, that has been implanted in the vascular system of a patient, comprising the steps of:

(a) percutaneously inserting first and second recovery tubes into vessels of the patient's vascular system that lead to both ends of the implanted filter;

(b) advancing the recovery tubes through the patients vascular system to where the distal ends of the recovery tubes are in the vicinity of the ends of the implanted filter;

(c) providing coupling mechanisms, that are complementary to the filter coupling mechanisms, on the distal ends of said first and second elongated members;

(d) advancing the first and second elongated members through the recovery tubes until the complementary coupling mechanisms on the ends of the filter and on the distal ends of the first and second elongated members are adjacent;

(e) manipulating the first and second elongated members from their proximal ends to cause the adjacent coupling mechanisms on the ends of the filter and the distal ends of the first and second elongated members to become attached;

(f) applying and maintaining a pressure in the proximal direction on the first and second elongated members;

(g) advancing one of said recovery tubes toward the filter such that it moves relative to its corresponding elongated member and over an end of the filter such that a portion of the filter is collapsed and contained within said one of said recovery tubes;

(h) advancing the other of said recovery tubes toward the filter such that it moves relative to its corresponding elongated member and over its corresponding end of the filter and the distal end of the said one of said recovery tubes such that the entire filter is contained within said other of said recovery tubes;

(i) releasing the coupling mechanisms between the filter and the elongated member that is within said one of said recovery tubes;

(j) withdrawing said one of said recovery tubes and its corresponding elongated member from the patient; and (k) withdrawing said other of said recovery tubes containing the entire filter and its corresponding first elongated member from the patient.

12. The method as set forth in claim 11 in which the filter is further of the type that has first and second units that are spaced longitudinally and connected by a resilient member and wherein step (f) causes the resilient member to expand and the first and second units to move longitudinally relative to each other.

13. The method as set forth in claims 11 or 12 wherein step (c) includes the following sub steps:

(1) doubling a first cord over upon itself so that the cord has a loop at one end;

(2) advancing the first cord, loop end first, through the first elongated member from the proximal to the distal end, until the loop exits the first elongated member at the distal end and functions as the coupling mechanism on one end of the first elongated member.

(3) doubling a second cord over upon itself so that the cord has a loop at one end;

(4) advancing the second cord, loop end first, through the second elongated member from the proximal to the distal end, until the loop exits the second elongated member at its distal end and functions as the coupling mechanism on one end of the second elongated member.

14. The method as set forth in claims 12 wherein step (i) includes the following sub steps:

(1) releasing one end of the cord that exits the proximal end of the second elongated member;

(2) pulling on the other end of the cord that exits the proximal end of the second elongated member until the released end of the cord is pulled into the second elongated member, thus releasing the coupling mechanisms.

15. The method as set forth in claims 12 or 14 in which the coupling mechanisms provided on the filter and in step (c) are made of radiopaque type material that can be seen on a fluoroscope to thus aid in completing the coupling process.

* * * * *